(12) United States Patent
Grace (10) Patent No.: US 9,445,819 B2
(45) Date of Patent: Sep. 20, 2016

(54) VENOUS NITINOL EMBOLIZATION INSERTS

(75) Inventor: Karl F. Grace, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 448 days.

(21) Appl. No.: 12/982,572

(22) Filed: Dec. 30, 2010

(65) Prior Publication Data

US 2012/0172908 A1 Jul. 5, 2012

(51) Int. Cl.
*A61M 29/00* (2006.01)
*A61B 17/12* (2006.01)
*A61B 17/00* (2006.01)
*A61B 17/22* (2006.01)
(Continued)

(52) U.S. Cl.
CPC ..... *A61B 17/12036* (2013.01); *A61B 17/1219* (2013.01); *A61B 17/12109* (2013.01); *A61B 17/12163* (2013.01); *A61B 17/12172* (2013.01); *A61B 17/12181* (2013.01); *A61B 2017/003* (2013.01); *A61B 2017/1205* (2013.01); *A61B 2017/22038* (2013.01); *A61B 2090/3966* (2016.02); *A61M 2025/0004* (2013.01); *A61M 2025/0681* (2013.01)

(58) Field of Classification Search
CPC ............ A61B 17/12036; A61B 17/1204; A61B 17/12172; A61B 17/12027; A61B 17/12045; A61B 17/12131; A61B 17/12145; A61B 17/1215; A61B 17/12154; A61B 17/12163; A61B 17/12168; A61B 17/12177; A61B 17/12181; A61B 17/12186; A61B 17/1219; A61B 17/12195; A61B 17/12109; A61B 17/12118; A61B 17/12122; A61F 2/06; A61F 2/90; A61F 2002/068; A61F 2002/823; A61F 2002/826; A61F 2002/828; A61F 2/04; A61F 2/07; A61F 2/82; A61F 2/852; A61F 2/856; A61F 2/86; A61F 2/89; A61F 2/91; A61F 2/915; A61F 2/92; A61F 2/93; A61F 2/94; A61F 2/95; A61F 2/954; A61F 2/958; A61F 2/962; A61F 2002/061; A61F 2002/065; A61F 2002/067; A61F 2002/91508; A61F 2002/91516; A61F 2002/91525; A61F 2002/91533; A61F 2002/91541; A61F 2002/9155; A61F 2002/91566; A61F 2002/91575; A61F 2002/91583
USPC ....... 606/191–192, 194, 200; 623/1.11–1.12, 623/1.15
See application file for complete search history.

(56) References Cited

U.S. PATENT DOCUMENTS

| 6,238,403 B1 | 5/2001 | Greene, Jr. et al. |
| 6,245,090 B1 | 6/2001 | Gilson et al. |
| 6,979,344 B2 | 12/2005 | Jones et al. |

(Continued)

FOREIGN PATENT DOCUMENTS

| WO | WO 2009086548 A1 * | 7/2009 |
| WO | WO 2009134337 A1 * | 11/2009 |

*Primary Examiner* — Jonathan Miles
*Assistant Examiner* — Kendra Obu
(74) *Attorney, Agent, or Firm* — Brinks Gilson & Lione (57) ABSTRACT

A venous nitinol embolization insert for restricting blood flow includes a tubular member and an embolization material attached to the tubular member. The embolization insert provides a predetermined blood flow rate based on experimental data. A method of controlling restriction of blood flow to a targeted vascular site within a patient's body includes selecting an insert that provides a predetermined blood flow rate corresponding to a desired blood flow rate. The embolization insert is selected from a plurality of embolization inserts that provide varied blood flow rates.

16 Claims, 7 Drawing Sheets

(51) Int. Cl.
*A61M 25/00* (2006.01)
*A61M 25/06* (2006.01)

(56) References Cited

U.S. PATENT DOCUMENTS

| | | | |
|---|---|---|---|
| 7,048,014 B2 | 5/2006 | Hyodoh et al. | |
| 2003/0032976 A1* | 2/2003 | Boucek | 606/200 |
| 2003/0199887 A1 | 10/2003 | Ferrera et al. | |
| 2004/0143288 A1* | 7/2004 | Searle | 606/200 |
| 2005/0192616 A1* | 9/2005 | Callister et al. | 606/193 |
| 2006/0085028 A1* | 4/2006 | Boock | 606/200 |
| 2009/0005860 A1* | 1/2009 | Gale et al. | 623/1.44 |
| 2009/0148492 A1* | 6/2009 | Dave et al. | 424/423 |
| 2009/0204143 A1* | 8/2009 | Park et al. | 606/200 |
| 2010/0106240 A1* | 4/2010 | Duggal et al. | 623/1.15 |
| 2010/0131002 A1* | 5/2010 | Connor et al. | 606/200 |
| 2010/0228184 A1* | 9/2010 | Mavani et al. | 604/35 |
| 2011/0046658 A1* | 2/2011 | Connor | A61B 17/12022 606/200 |

* cited by examiner

VENOUS NITINOL EMBOLIZATION INSERTS

FIELD

The present invention generally relates to medical devices, and more particularly to embolization devices.

BACKGROUND

A number of different devices may be used to occlude a body cavity including, for example, a blood vessel. An example of an occlusion device includes embolization coils. It is known to cut off blood supply to site of tumors to kill the tumors. Current embolization methods and devices make it difficult to determine the degree of embolization.

To determine the condition of embolization, a blood pressure monitoring means may be used with a catheter to monitor blood pressure at the target site during embolization. The blood pressure monitoring means, however, cannot repair the embolization when insufficient embolization or over-embolization occurs at the target site. Insufficient embolization may be ineffective or unacceptably slow in accomplishing the desired outcome. Over-embolization may result in patient discomfort or pain or other complications. When insufficient embolization or over-embolization occurs, the clinician will need to retrieve the occlusion device that is already placed in patient's body and replace it with another occlusion device to ensure proper embolization.

Moreover, the typical embolization methods and devices may involve undesirable partial migration of the occlusion device or mis-embolization (i.e., embolization of non-target vessels).

SUMMARY

In one form, a medical system for controlling blood flow within a blood vessel according to the present disclosure includes an embolization insert that allows for a predetermined blood flow rate within the blood vessel. The embolization insert includes a tubular member and an embolization material attached to the tubular member.

In another form, a method of controlling restriction of blood flow to a targeted vascular site within a patient's body includes selecting an embolization insert that allows for a predetermined blood flow rate, and deploying the embolization insert within a blood vessel to restrict blood flow to the predetermined blood flow rate.

Further features and advantages of the invention will become readily apparent from the following description and from the claims.

DETAILED DESCRIPTION

Figure 1:
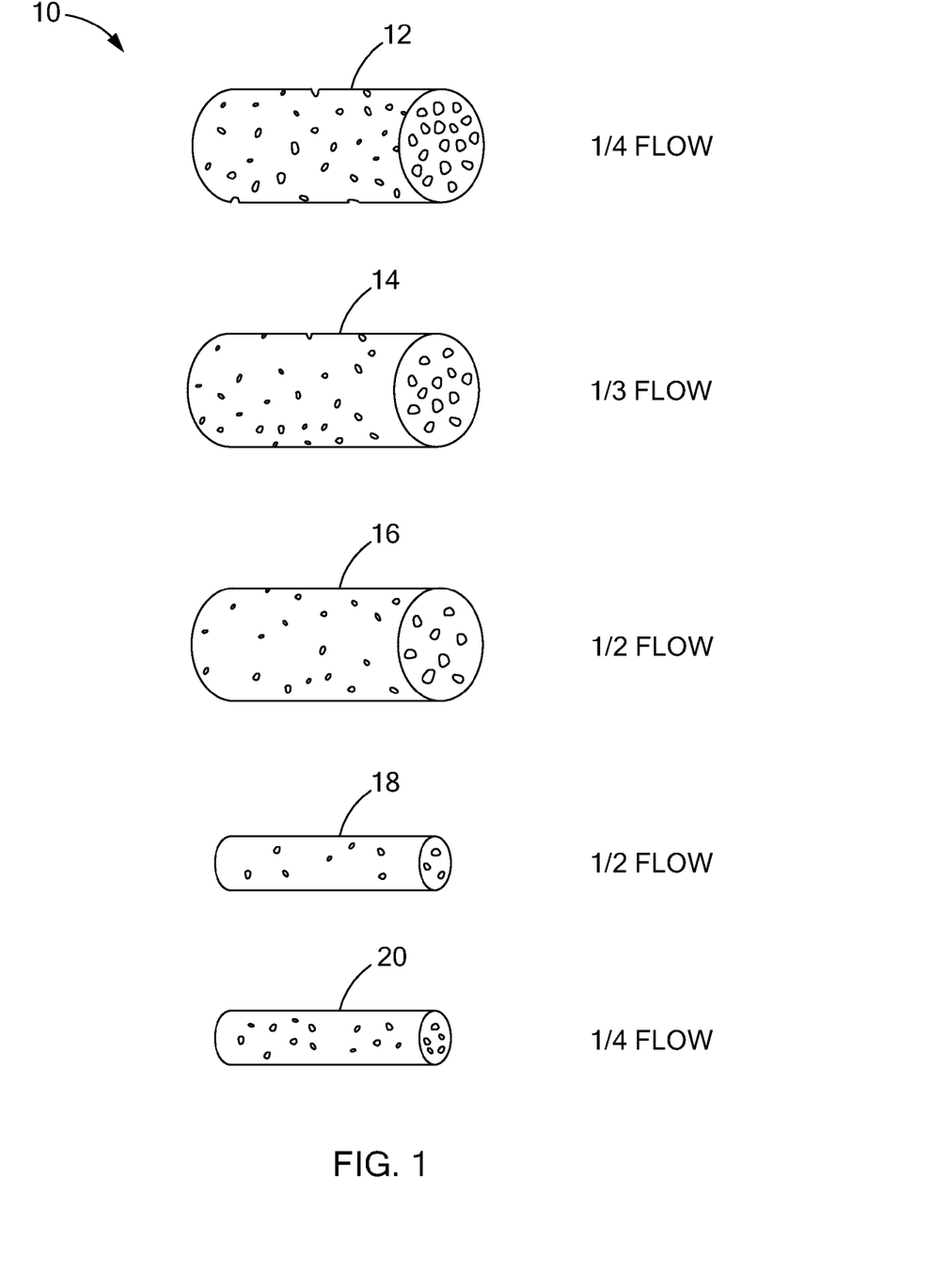
FIG. 1 is a perspective view of an embolization device including a plurality of embolization inserts in accordance with an embodiment of the present disclosure.

Referring now to FIG. 1, an embolization device according to the teachings of the present disclosure is generally designated by reference number 10. The embolization device 10 includes a plurality of embolization inserts 12, 14, 16, 18, 20 that provide varied blood flow rates through the embolization inserts 12, 14, 16, 18 and 20. While five embolization inserts 12, 14, 16, 18, 20 are shown, it is understood that the embolization device 10 may include any number of embolization inserts having the same or different sizes to provide the same or varied flow rates for different applications. For example only, the embolization inserts 12, 14, 16 have the same diameter to provide different degrees of blood flow reduction in a first blood vessel, whereas the embolization inserts 18 and 20 provide different degrees of blood flow reduction in a second blood vessel that is smaller than the first blood vessel. The embolization inserts 12, 14, 16, 18 and 20 are designed to provide a flow rate that is ¼, ⅓, or ½ a flow rate of an unrestricted blood flow to a target site when the blood has a nominal specific gravity and nominal blood pressure. Therefore, when a patient's blood has a nominal specific gravity and the nominal blood pressure, the embolization insert 12 allows for ¼ blood flow to a target site while restricting ¾ blood flow compared with 100% blood flow in the absence of the embolization insert 12. The embolization insert 16 reduces the blood flow by half compared with 100% blood flow in the absence of the embolization insert 16.

Figure 2:
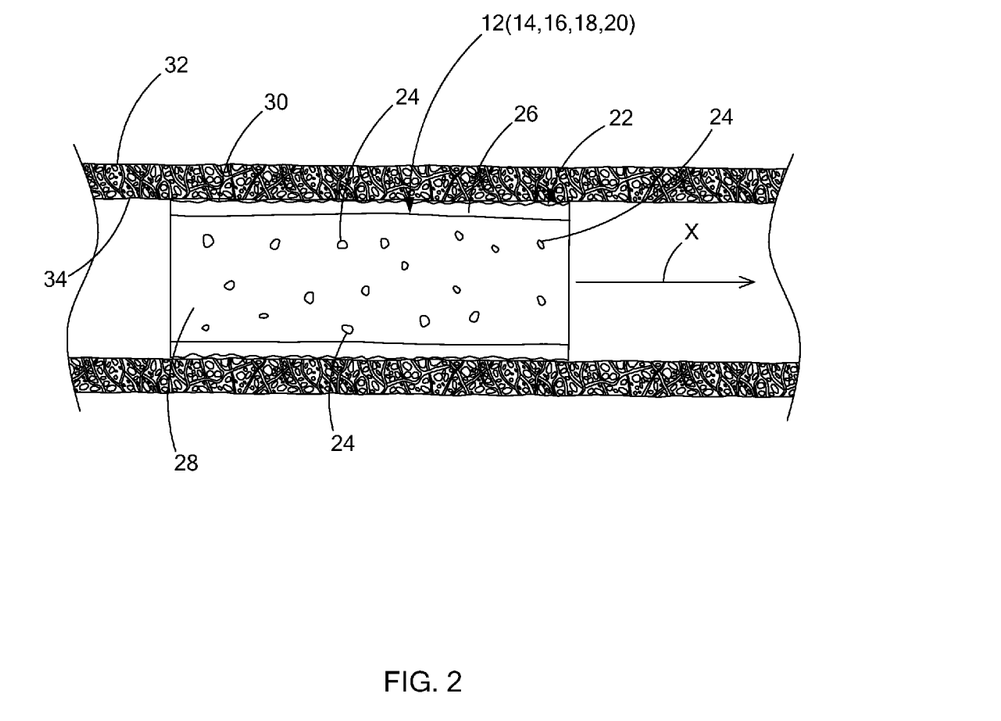
FIG. 2 is a cross-sectional environmental view of an embolization insert of FIG. 1 in a body vessel.

Referring to FIG. 2, the embolization inserts 12, 14, 16, 18 and 20 each include a tubular member 22 and an embolization material 24. The tubular member 22 includes a tubular wall 26 defining a lumen 28 extending along a longitudinal axis X of the tubular member 22. The tubular wall 26 has a porous mesh structure configured to result in little or no flow restriction. The tubular member 22 may have a roughed outer surface 30 for contacting the inner wall 34 of the blood vessels 32 to reduce movement of the embolization inserts 12, 14, 16, 18, 20 after the embolization inserts are placed in the blood vessels 32. The tubular member 22 may have a Nitinol tubular structure and may be expandable between a collapsed state and an expanded state.

The embolization material 24 is attached to the tubular member 22 and may include a plurality of spherical particles for restricting blood flow. In one example, the embolization material 24 is enclosed in the tubular member 22 and dispersed within the lumen 28 of the tubular member 22. Alternatively, the embolization material 24 may be embedded into the tubular wall 26. The blood flow rate allowed by the embolization inserts 12, 14, 16, 18 20 depends on the volume/weight of the embolization material 24 retained in the tubular member 22. The embolization inserts 12, 14, 16, 18, 20 may be venous inserts that provide pre-set amounts of blood flow restriction for use in embolization procedures. The spherical particles of the embolization material 24 function to limit blood flow through the embolization inserts 12, 14, 16 18, 20. In one example, the embolization material 24 includes but is not limited to, Acryl microspheres, Hydrogel-Polyzene F microspheres, $^{90}$Y microspheres, gelfoam, microfibrillar collagen, glue or fibers.

In at least one embodiment, the embolization particles may be coated with a medicant. The medicant coating may be sprayed via a coating spray device. The thickness of the coating may be relatively thin, such as for example, on the order of several angstroms, however, thicker coatings may be used without departing from the present invention. Further details of embolization particles may be found in U.S. patent application Ser. No. 12/193,368, filed Aug. 18, 2008, the entire contents of which are incorporated herein.

Referring back to FIG. 1, the plurality of embolization inserts 12, 14, 16, 18 and 20 may have different diameters to fit in blood vessels/veins of different sizes. For example, the embolization inserts 12, 14 and 16 have larger diameters for larger blood vessels/veins, whereas the embolization inserts 18 and 20 have smaller diameters for smaller blood vessels/veins. Generally, the diameters of the inserts are approximately equal to the size of the blood vessels so that the embolization inserts may be properly inserted in the blood vessels and positioned at the target site. The embolization inserts 12 and 20 have different diameters to fit in different blood vessels but can provide the same degree of blood restriction.

The flow rate depends on volume/weight of the embolization materials contained in the embolization inserts 12, 14, 16, 18, 20. An embolization insert having a higher volume/weight of embolization material provides more restricted blood flow (i.e., lower blood flow rate). The relationship between the blood flow rate and the volume/weight of the embolization material 24 may be predetermined based on a lookup table that includes experimental data. The relationship between a patient's blood pressure and a desired blood flow rate after embolization may also be determined based on experimental data. Therefore, a desired embolization may be achieved by determining a desired blood flow rate based on a patient's blood pressure, followed by selecting an embolization insert that provides the desired blood flow rate. No pressure monitoring means is needed during the embolization procedure to ensure a proper embolization.

Figure 3:
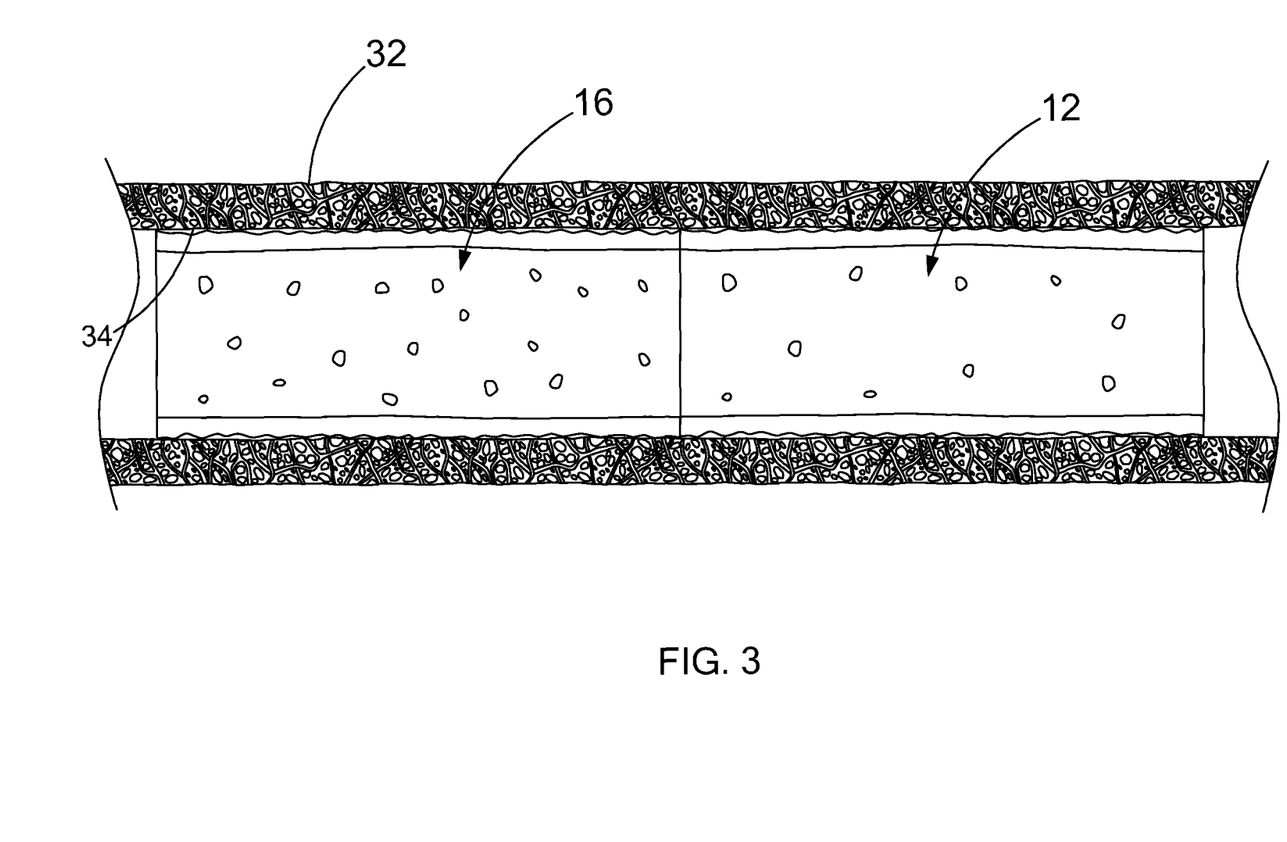
FIG. 3 is a cross-sectional environmental view of an alternate form of embolization inserts of FIG. 1 in a body vessel.

Referring to FIG. 3, more than one embolization inserts 12, 14, 16, 18, 20 may be consecutively deployed within the blood vessel 32 adjacent to a target site to restrict blood flow through the target site. FIG. 3 shows the embolization inserts 12 and 16 having the same diameter but different flow rate are arranged in series in the same blood vessel 32 for controlled flow rate. For example, the embolization insert 12 may allow for ¼ blood flow, whereas the embolization insert 16 may allow for ½ blood flow. The embolization inserts 12 and 16 may jointly allow for ⅛ blood flow.

Figure 4:
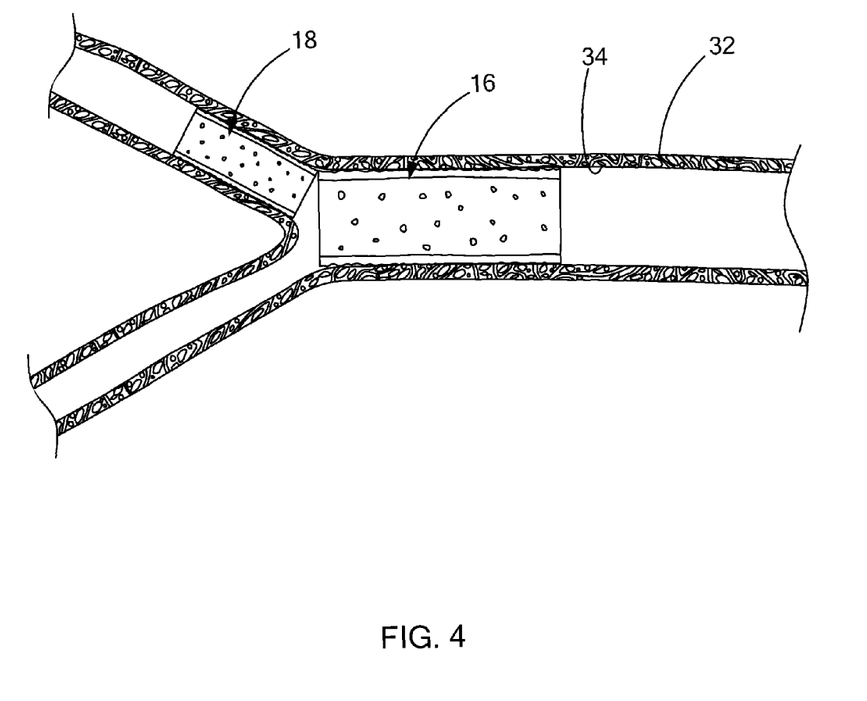
FIG. 4 is a cross-sectional environmental view of another alternate form of embolization inserts of FIG. 1 in a body vessel.

FIG. 4 shows that the embolization inserts 16 and 18 having different diameters may be placed in blood vessels of different sizes. The embolization insert 18 having a smaller diameter may be placed in one branch of the blood vessel, whereas the embolization insert 16 having a larger diameter may be placed in the main blood vessel. The embolization inserts 16 and 18 each restrict ½ blood flow and thus jointly restrict the blood flow to ¼ blood flow.

Figure 5:
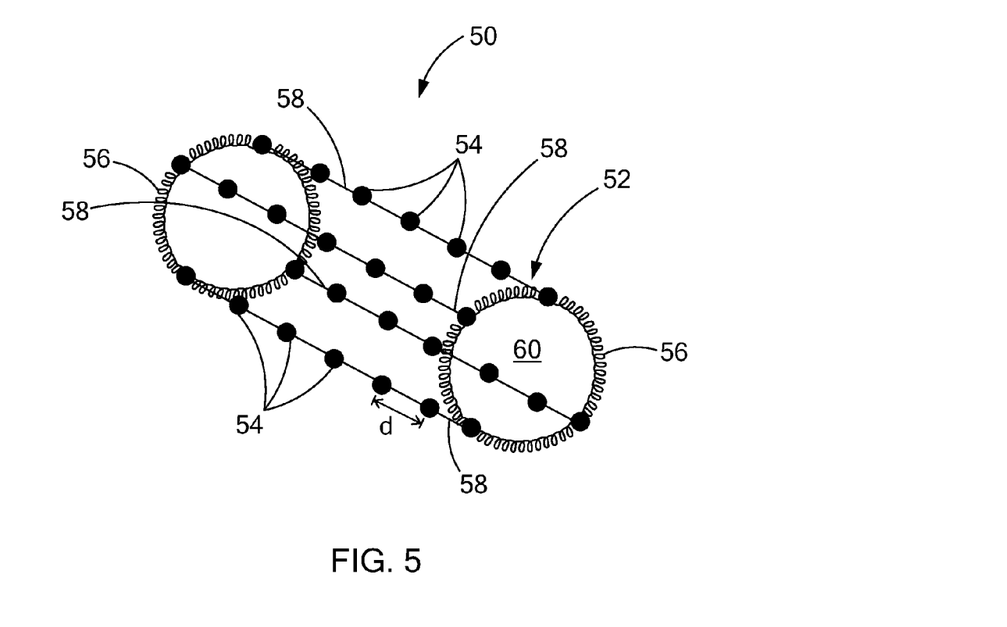
FIG. 5 is a schematic perspective view of an alternate form of an embolization insert.

Referring to FIG. 5, an alternate form of an embolization insert 50 includes a tubular member 52 and a plurality of embolization spheres or beads 54. The tubular member 52 includes opposing ring members 56 and a plurality of longitudinal struts 58 disposed between the opposing ring members 56 and spaced apart along a circumferential direction of the ring members 56. The ring members 56 may be barbed rings. The distance between the longitudinal struts 58 along the circumferential direction of the ring members 56 and consequently the number of the longitudinal struts 58 may be varied depending on desired degree of blood flow reduction. For example, an embolization insert for a more restricted blood flow may include more longitudinal struts than one for a less restricted flow.

The diameter of the ring members 56 depends on a diameter of the blood vessel in which the embolization insert 50 is to be inserted. For example, the diameter of the ring members 56 is equal to or slightly greater than the diameter of the blood vessel when the embolization insert 50 is in the expanded state. The tubular member 52 defines a passageway 60 therein. The plurality of embolization spheres 56 are attached to the opposing ring members 56 and/or the plurality of struts 58 at a predetermined interval d.

Figure 6:
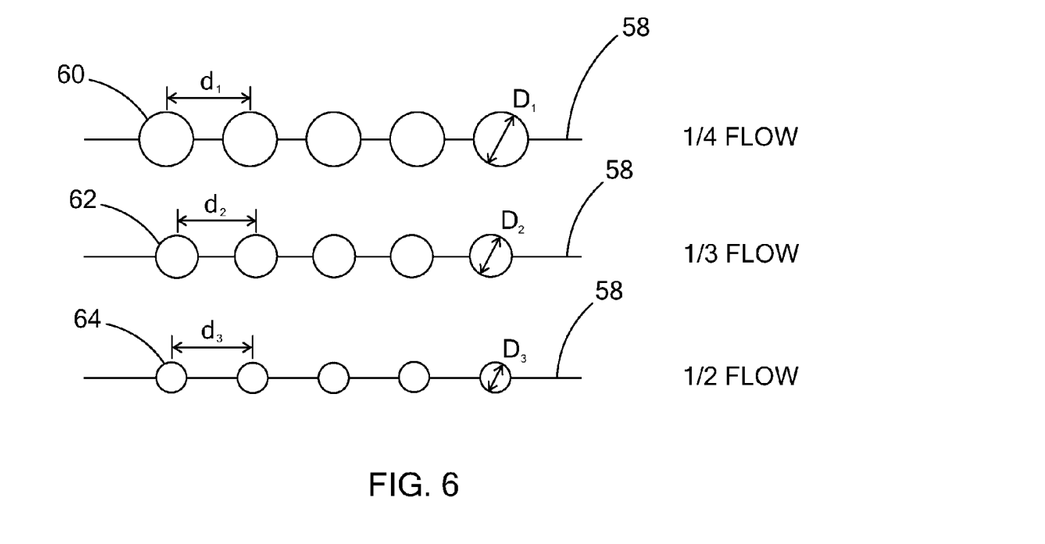
FIG. 6 is a comparison of diameters and intervals of embolization spheres for different degrees of blood flow reduction.

Referring to FIG. 6, the diameter D and intervals d of the embolization spheres 54 may be varied for different degrees of blood flow reduction. An embolization insert for ¼ flow (i.e., a reduced blood flow that is ¼ the unrestricted flow) may have spheres 60 having a diameter of D1 and attached to the longitudinal struts 58 at a first interval d1. An embolization insert for ⅓ flow (i.e., a reduced blood flow that is ⅓ the unrestricted flow) may have spheres 62 having a diameter of D2 and attached to the longitudinal struts 58 at a second interval d2. An embolization insert for ½ flow (i.e., a reduced blood flow that is ½ the unrestricted blood flow) may have spheres 64 having a diameter of D3 and attached to the longitudinal struts 58 at a third interval d3. In one example, the diameters D1, D2, D3 of the spheres 60, 62, 64 and the intervals d1, d2, d3 may satisfy the following relationship:

$$D1 > D2 > D3 \text{ and } d1 \leq d2 \leq d3.$$

In another example, the diameters D1, D2, D3 of the spheres 60, 62, 64 and the intervals d1, d2, d3 may satisfy the following relationship:

$$D1 = D2 = D3 \text{ and } d1 < d2 < d3.$$

It is understood that the diameters D1, D2, D3 and the intervals d1, d2, d3 of the spheres 60, 62, 64 for different degrees of blood flow reduction are not limited to the above relationship. The diameters D1, D2, D3 and intervals d1, d2, d3 of the spheres 60, 62, 64 may be properly selected to occupy a portion of the passageway 60 so that the passageway 60 is reduced for varied degrees of blood flow reduction.

The embolization spheres 54 may include embolizing agent, such as, Acryl microspheres, Hydrogel-Polyzene F microspheres, $^{90}$Y microspheres, or microfibrillar collagen.

Figure 7:
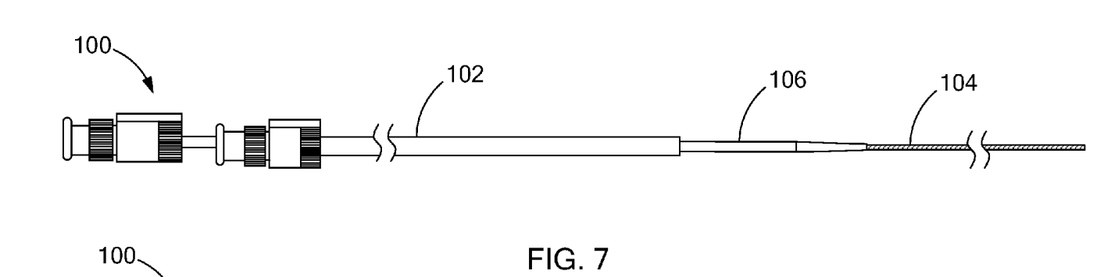
FIG. 7 is a side view of one embodiment of a delivery and retrieval assembly for use with the embolization device of the present disclosure.
Figure 8:
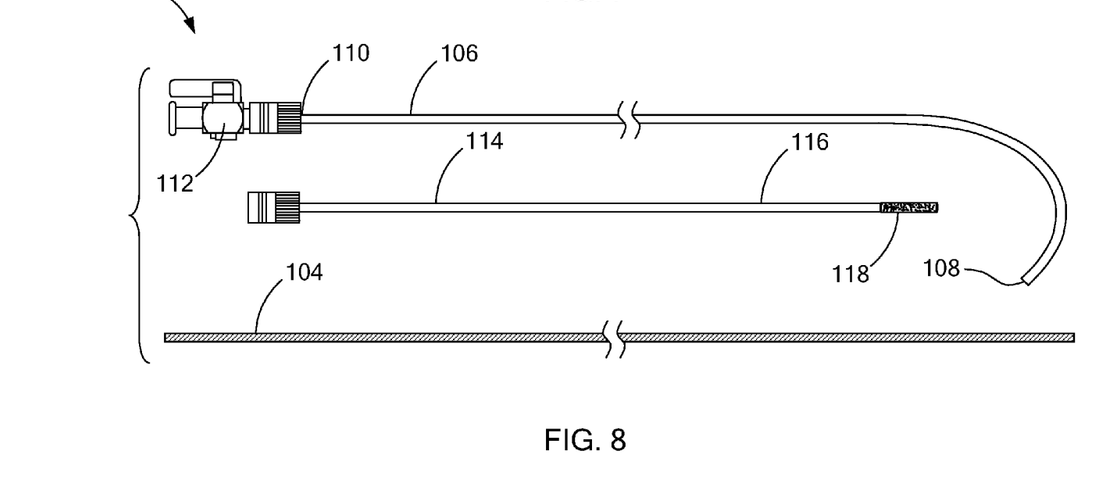
FIG. 8 is an exploded view of the delivery and retrieval assembly of FIG. 7.

FIGS. 7 and 8 depict a delivery assembly 100 for introducing and retrieving the embolization insert for embolizing a body vessel according to the teachings of the present disclosure. As shown, the delivery assembly 100 includes a polytetrafluoroethylene (PTFE) introducer sheath 102 for percutaneously introducing an outer sheath 106 into a body vessel. Any other suitable material for the introducer sheath 102 may be used without falling beyond the scope or spirit of the present invention. The introducer sheath 102 may have any suitable size, for example, between about 3-French to 8-French. The introducer sheath 102 serves to allow the outer sheath 106 and an inner member, stylet or catheter 114 to be percutaneously inserted to a desired location in the body vessel. The introducer sheath 102 receives the outer sheath 106 and provides stability to the outer sheath 106 at a desired location of the body vessel. For example, the introducer sheath 102 is held stationary within a common visceral artery, and adds stability to the outer sheath 106, as the outer sheath 106 is advanced through the introducer sheath 102 to an occlusion area in the vasculature.

As shown, the assembly 100 may also include a wire guide 104 configured to be percutaneously inserted within the vasculature to guide the outer sheath 106 to the embolization area. The wire guide 104 provides the outer sheath 106 with a path to follow as it is advanced within the body vessel. The size of the wire guide 104 is based on the inside diameter of the outer sheath 106 and the diameter of the target body vessel.

When a distal end 108 of the outer sheath 106 is at the desired location in the body vessel, the wire guide 104 is removed and an embolization insert 118, having a proximal segment releasably coupled to a distal portion 116 of the inner catheter 114, is inserted into the outer sheath 106. The inner catheter 114 is advanced through the outer sheath 106 for deployment of the device through the distal end 108 to occlude the body vessel during treatment of, for example, an aneurism. In this example, the distal portion 116 is shown including an embolization insert 118.

The outer sheath 106 further has a proximal end 110 and a hub 112 to receive the inner catheter 114 and device to be advanced therethrough. The size of the outer sheath 106 is based on the size of the body vessel in which it percutaneously inserts, and the size of the device.

In this embodiment, the embolization insert 118 and the inner catheter 114 are coaxially advanced through the outer sheath 106, following removal of the wire guide 104, in order to position the embolization insert 118 to occlude the body vessel 32. The device is guided through the outer sheath 106 by the inner catheter 114, preferably from the hub 112, and exits from the distal end 108 of the outer sheath 106 at a location within the vasculature where occlusion is desired.

Likewise, this embodiment may also retrieve the device by positioning the distal end 108 of the outer sheath 106 adjacent the deployed device in the vasculature. The inner catheter 114 is advanced through the outer sheath 106 until the distal portion 116 protrudes from the distal end 108 of the outer sheath 106. The distal portion 116 is coupled to a proximal end of the device, after which the inner catheter 114 is retracted proximally, drawing the device into the outer sheath 106.

Figure 9:
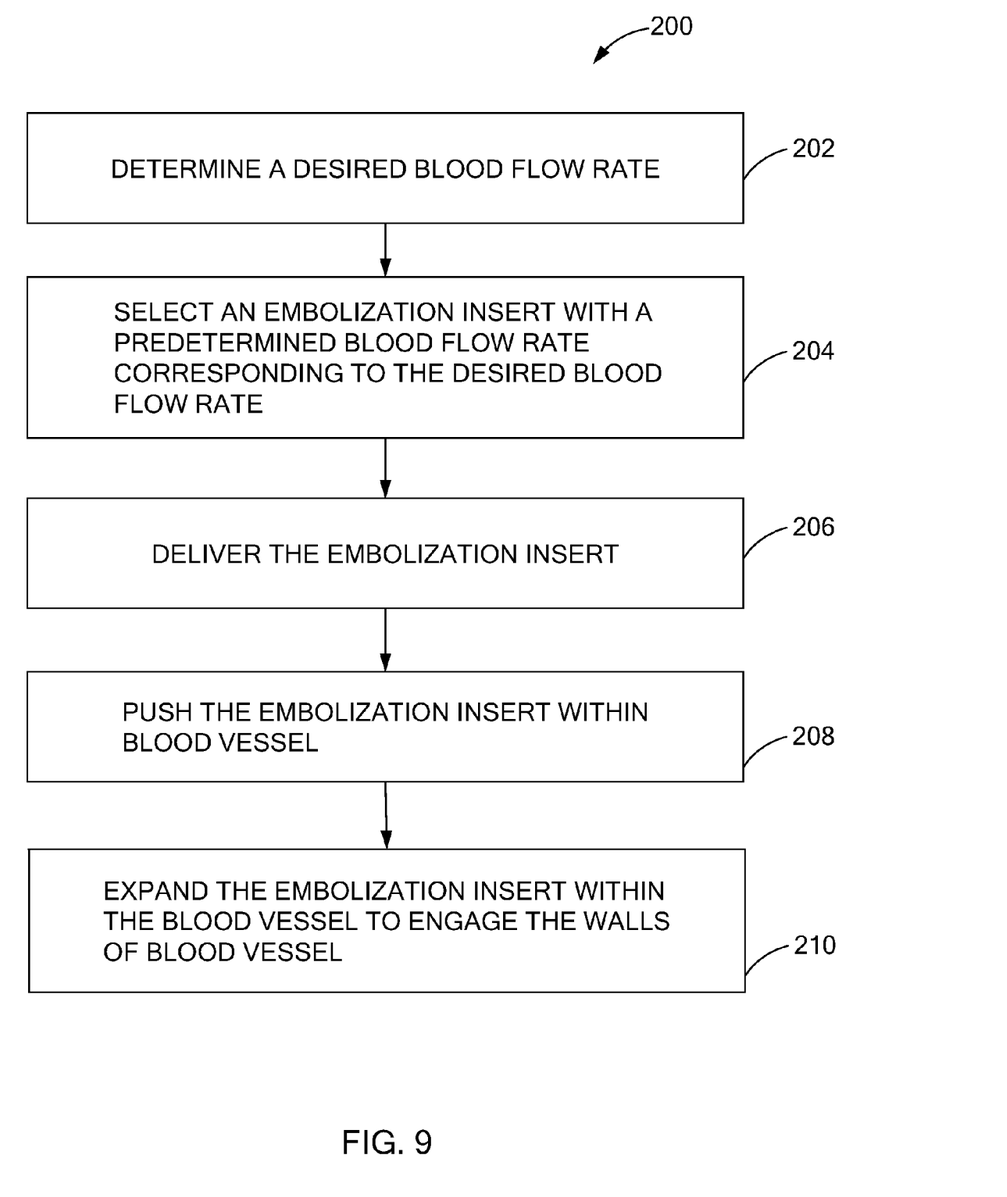
FIG. 9 is a flow-chart describing a method of controlling restriction of blood flow using an embolization device according to the present disclosure.

Referring to FIG. 9, a method 200 of controlling restriction of blood flow to a targeted vascular site, such as a blood vessel, within a patient's body is shown. A desired blood flow rate is determined in step 202. The desired blood flow rate is determined based on a patient's body condition including condition of the target site and the patient's specific physiology for an effective treatment of the patient. The patient's specific physiology to be evaluated includes, but is not limited to, blood specific gravity, blood pressure, blood thickness and blood flow to the target site. For example, the clinician may determine the desired blood flow rate based on a patient's prevailing blood pressure. Therefore, if the patient has low blood pressure, an embolization insert that allows for a higher flow rate may be placed. If the patient has high blood pressure, an embolization insert allows for lower flow rate may be placed.

Next, an embolization insert that allows for a predetermined blood flow rate corresponding to the desired blood flow rate is selected in step 204. Alternatively, a plurality of embolization inserts that jointly provide the predetermined blood flow rate may be selected.

Later, the embolization insert that provides the predetermined blood flow rate is delivered and deployed by using any of the conventional embolization methods in step 206. In one example, the embolization insert is delivered through a radiopaque-tipped catheter under fluoroscopy. A pusher wire is used to push out the embolization insert when the distal end of the catheter is at the desired embolization location in step 208. The embolization insert is expanded within the body vessel to engage the walls of the body vessel in step 210.

When more than one inserts are selected, the embolization may be achieved by placing a plurality of inserts in series. The embolization inserts are inserted consecutively within the blood vessel to selectively restrict blood flow within the blood vessel in a controlled manner. Therefore, the embolization procedure is performed in a fine-tune manner to successively achieve the desired degree of embolization, or the desired restriction of blood flow.

If a clinician decides to deploy more than one embolization insert in series for additional blood flow reduction, the total amount of the blood reduction may not be additive, multiplicative, or even exponential. For example, a embolization insert providing ½ flow rate followed in series by another embolization insert providing ⅓ flow rate may not result in a blood flow reduction to ⅙ (i.e., ½×⅓) but a near-complete embolization of 100%. Accordingly, it is recommended that a slightly less restrictive embolization insert be inserted initially. If the desired restriction is not achieved, the clinician has the option of replacing the device with a more restrictive one or inserting an additional device proximally on the upstream side of the first embolization insert. The second embolization insert may need to be much less restrictive than the first embolization insert to fine-tune the embolization.

With the embolization procedure of the present disclosure, there is no need to use additional pressure monitoring means to monitor the blood pressure because the embolization inserts are designed and have been tested to provide the desired blood flow rate.

The blood pressure of the patient may change over time after the embolization is completed. When the patient's blood pressure increases, the embolization insert that is already placed may be replaced with another embolization insert with a lower flow rate. Alternately, another insert may be added to reduce the blood flow rate. When the patient's blood pressure decreases, the insert(s) that is/are already placed in the blood vessel may be retrieved and replaced with an embolization insert with a higher flow rate.

The embolization device in accordance with the teachings of the present disclosure provide a way to control blood flow to a target site, for example, where a tumor is located, to control growth of the tumor. The embolization device "fine tunes" the embolization by cutting off the blood flow in a controlled manner, as opposed to a conventional method that completely blocks the blood flow.

It is understood that the assembly described above is merely one example of an assembly that may be used to deploy the occlusion device in a body vessel. Of course, other apparatus, assemblies and systems may be used to deploy any embodiment of the occlusion device without falling beyond the scope of the following claims.

The invention claimed is:

1. A medical system for controlling blood flow within a blood vessel, the medical system comprising:

a tubular member having a tubular wall and a single lumen extending along a longitudinal axis of the tubular member; and embolization material that allows for a predetermined blood flow rate within the blood vessel, wherein the embolization material is placed within the single lumen of the tubular member and includes a plurality of flow reduction material particles made of material that is stable in the blood flow, the flow reduction material particles occupying a particle volume decreasing a free volume inside the tubular member, the flow reduction material particles being spherical and dispersed substantially throughout the entire single lumen of the tubular member, the particle volume corresponding to a predetermined degree of axial blood flow reduction through the tubular member, wherein the predetermined blood flow rate is greater than zero.

2. The medical system of claim 1, wherein the tubular member defines a porous mesh structure.

3. The medical system of claim 1, wherein the tubular member defines a rough outer surface.

4. The medical system of claim 1, wherein the predetermined blood flow rate is determined based on experimental data.

5. The medical system of claim 1, wherein the tubular member and embolization material define at least one flow reduction insert, the at least one flow reduction insert comprising a plurality of flow reduction inserts that include varied particle volumes for varied blood flow rates within the blood vessel.

6. The medical system of claim 5, wherein the plurality of flow reduction inserts have different diameters to fit in different sizes of blood vessels.

7. The medical system of claim 5, wherein at least two of the plurality of flow reduction inserts have the same diameter and contain different particle volumes to allow for different blood flow rates.

8. The medical system of claim 1, wherein the plurality of spherical flow reduction material particles are spaced at a predetermined interval based on the degree of blood flow reduction.

9. A method of controlling restriction of blood flow to a targeted vascular site within a patient's body, the method comprising:

determining a desired blood flow rate at the targeted vascular site based on a body condition of a patient;

selecting a medical system for controlling restriction of blood flow, the system comprising:

at least one cylindrical flow reduction insert that allows for a predetermined blood flow rate corresponding to the desired blood flow rate from a plurality of different flow reduction inserts, the at least one cylindrical flow reduction insert comprising a tubular member and embolization material, the tubular member having a tubular wall and a single lumen extending along a longitudinal axis of the tubular member, the embolization material being placed within the single lumen of the tubular member and including a plurality of flow reduction material particles made of material that is stable in the blood flow, the flow reduction material particles being spherical and dispersed substantially throughout the entire single lumen of the tubular member, the flow reduction material particles occupying a particle volume filling different portions of volume inside the plurality of different flow reduction inserts with different predetermined degrees of axial blood flow reduction through the plurality of different flow reduction inserts, wherein the predetermined blood flow rate is greater than zero; and deploying the at least one cylindrical flow reduction insert within the blood vessel to restrict blood flow to the desired blood flow rate.

10. The method of claim 9, wherein the predetermined blood flow rate is determined based on experimental data.

11. The method of claim 9, further comprising selecting the at least one flow reduction insert from a plurality of flow reduction inserts that provide varied blood flow rates.

12. The method of claim 9, further comprising selecting the at least one flow reduction insert from a plurality of inserts that have varied sizes to fit in blood vessels of different sizes.

13. The method of claim 9, further comprising deploying at least two of the flow reduction inserts consecutively within the blood vessel, wherein the at least two of the flow reduction inserts are arranged in series in the blood vessel.

14. The method of claim 13, wherein the at least two flow reduction inserts jointly allow for the predetermined blood flow rate.

15. The method of claim 9, wherein the body condition of the patient includes at least one of the patient's prevailing blood pressure, blood thickness, blood flow to the targeted vascular site, and condition of the targeted vascular site.

16. A medical system for controlling blood flow within a blood vessel, the medical system comprising:

a flow reduction insert that allows for a predetermined blood flow rate within the blood vessel, the flow reduction insert comprising a tubular member and embolization material, the tubular member having a tubular wall and a single lumen extending along a longitudinal axis of the tubular member, the embolization material being placed within the single lumen of the tubular member and including a plurality of flow reduction material particles made of material that is stable in the blood flow, the flow reduction material particles occupying a particle volume decreasing a free volume inside the tubular member, the flow reduction material particles being spherical and dispersed substantially throughout the entire single lumen of the tubular member, the particle volume corresponding to a predetermined degree of axial blood flow reduction through the tubular member, wherein the predetermined blood flow rate is greater than zero.

\* \* \* \* \*